US00PP09229P

United States Patent [19]

Trees

[11] Patent Number: Plant 9,229

[45] Date of Patent: Aug. 1, 1995

[54] GERANIUM PLANT NAMED 'STARBURST RED'

[75] Inventor: Scott C. Trees, Arroyo Grande, Calif.

[73] Assignee: Geo. J. Ball, Inc., West Chicago, Ill.

[21] Appl. No.: 341,913

[22] Filed: Nov. 15, 1994

[51] Int. Cl.[6] ..... A01H 5/00
[52] U.S. Cl. ..... Plt./87.12
[58] Field of Search ..... Plt. 87.12

*Primary Examiner*—James R. Feyrer
*Attorney, Agent, or Firm*—Burns, Doane, Swecker & Mathis

[57] ABSTRACT

A new and distinct *Pelargonium*×*hortorum* cultivar named Starburst Red is provided. This new Zonal Geranium cultivar was the result of a controlled breeding program wherein an unnamed plant designated 4077-1 was pollinated by the BSR-177 White cultivar (U.S. Plant Pat. No. 8,284). The new cultivar forms attractive multi-patterned single florets that are red, white, and pink in coloration. Attractive medium green foliage is well retained even during shipment. The growth habit is somewhat self-branching and does not require the use of a growth regulator.

2 Drawing Sheets

SUMMARY OF THE INVENTION

The present invention comprises a new and distinct Geranium cultivar, botanically known as *Pelargonium*-×*hortorum* Bailey, and hereinafter referred to by the cultivar name Starburst Red.

The new cultivar is a product of a planned breeding program which has as its objective the creation of a new Geranium cultivar that exhibits uniform flowers, medium green foliage, a medium self-branching growth habit that requires no growth regulator, a propensity for rapid rooting, and a stable foliage coloration during shipment.

The breeding program that resulted in the production of the new cultivar of the present invention was carried out in a controlled environment during 1989 at Arroyo Grande, Calif., U.S.A. The female parent (i.e., seed parent) was a plant designated 4077-1 (non-patented in the United States) which exhibits single purple and white striped florets and medium green foliage. The male parent (i.e. pollen parent) was the BSR-177 White cultivar (U.S. Plant Pat. No. 8,284) which exhibits semi-double white florets and dark green foliage. The parentage of new Starburst Red cultivar can be summarized as follows:

4077-1×BSR-177 White.

Starburst Red was discovered and selected during 1990 as a highly distinctive flowering plant from among the progeny of the stated cross at Arroyo Grande, Calif., U.S.A. This plant was initially designated BFP-738.

It was found that the new cultivar of the present invention:

(a) exhibits single multi-patterned red, white, and pink florets,
(b) forms medium green foliage with zonation, and
(c) exhibits a medium growth habit.

When a plant material of the Starburst Red cultivar is subjected to standard random amplified polymorphic DNA marker analysis (RAPD) using polymerase chain reaction (PCR) and a known set of DNA primers, it is found to exhibit a distinctive fingerprint map which is on file at the Ball FloraPlant Division of Geo. J. Ball, Inc. at Arroyo Grande, Calif., U.S.A.

The first act of asexual reproduction of the Starburst Red cultivar was accomplished when vegetative cuttings were taken from the initial selection in a controlled environment at Arroyo Grande, Calif., U.S.A. by a technician working under the direction and supervision of the originator of the new cultivar. Horticultural examination of plants resulting from such asexual propagation during 1990 has demonstrated that the combination of unique characteristics as herein described for the Starburst Red cultivar is firmly fixed and is retained through successive generations of such reproduction.

The new Starburst Red cultivar has not been observed under all possible environmental conditions. Accordingly, the described phenotype may vary somewhat with variations in the environment, such as temperature, light intensity, and day length.

The originator of this new cultivar is unaware of any commercial vegetatively produced cultivar which is in any way similar to the new Starburst Red cultivar. The new cultivar of the present inventor exhibits unique single florets with petals having coloration ranging from bright red through pale pink to white presented as stripes, freckles and patches as well as occasional whole petals of solid colors as illustrated in the accompanying photographs.

BRIEF DESCRIPTION OF THE PHOTOGRAPHS

The accompanying photographs show typical flower and foliage characteristics of the new Starburst Red cultivar with colors being as nearly true as it is reasonably possible to make the same in color illustrations of this character. The plants were being grown in greenhouses at West Chicago, Ill., U.S.A.

FIG. 1—illustrates the general appearance of an overall plant wherein five umbels are present.

FIG. 2—illustrates a close-up view of a single umbel.

FIG. 3—illustrates representative variations in petal coloration.

FIG. 4—illustrates additional representative variations in petal coloration.

DETAILED DESCRIPTION

Figure 1:
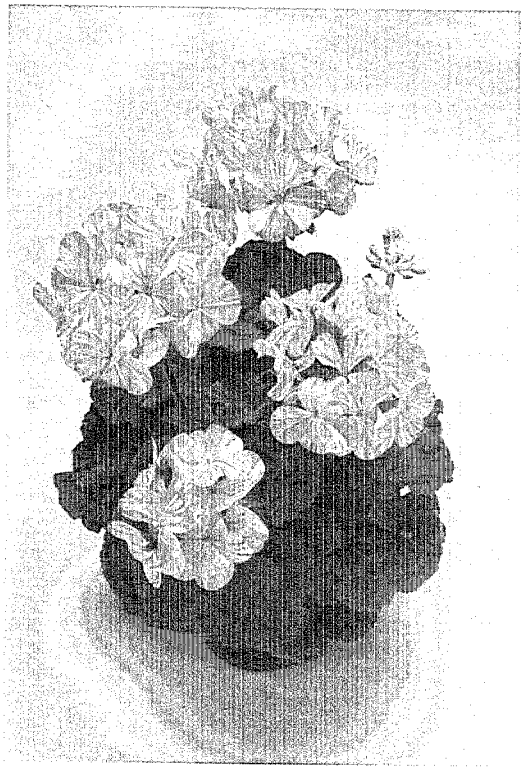
Figure 2:
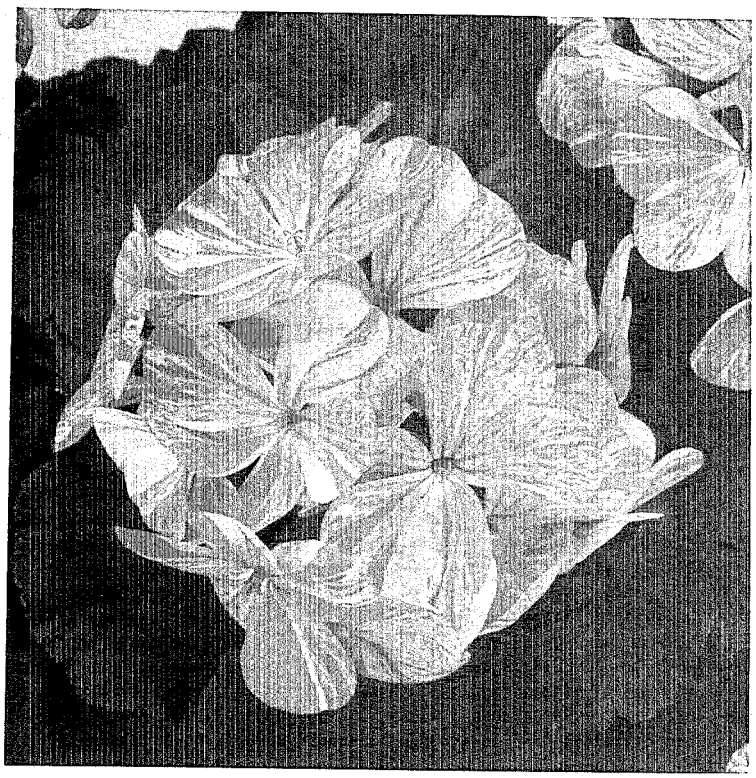
Figure 3:
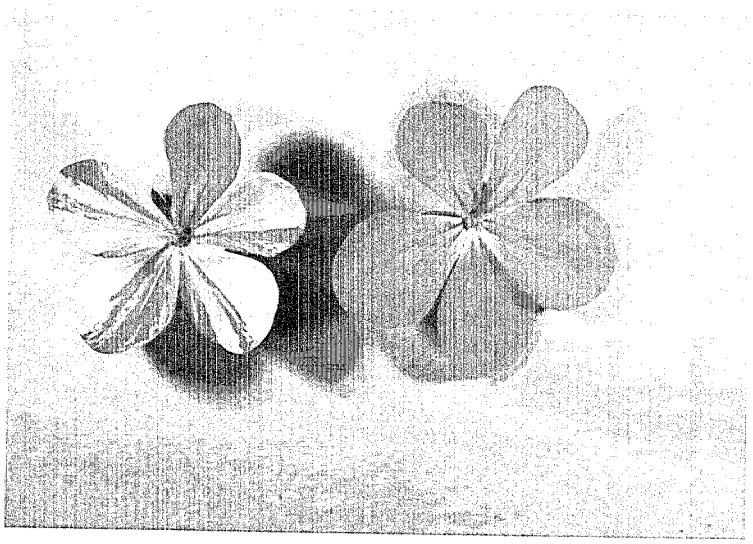
Figure 4:
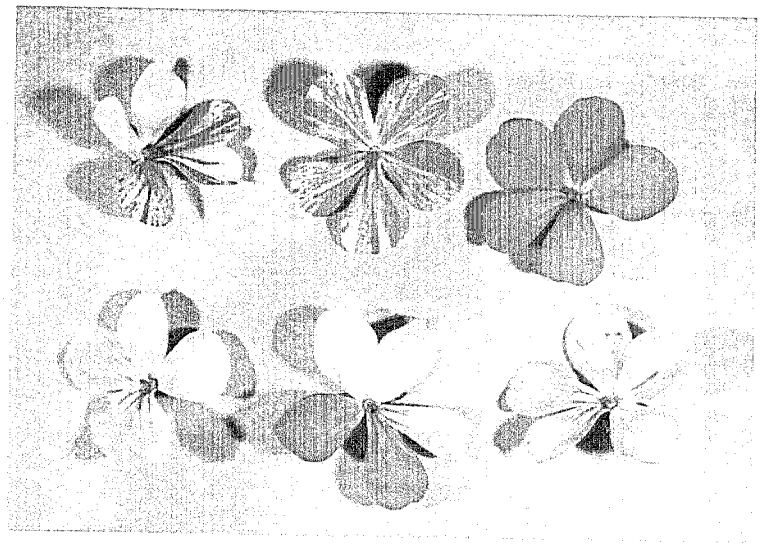

The following observations, measurements and comparisons describe plants grown in Ball FloraPlant's greenhouses located at West Chicago, Ill., U.S.A. under conditions which approximate those generally used in commercial practice. In the following description, color references are made to the R.H.S. Colour Chart of The Royal Horticultural Society, London, England. The color values were determined between 3:00 and 3:30 p.m. on Aug. 31, 1994, under natural light conditions of 150 footcandles.

Classification:

*Botanical.*—*Pelargonium*×*hortorum* Bailey, cv. Starburst Red.

*Commercial.*—Zonal Geranium.

INFLORESCENCE

A. Umbel:

*Average diameter.*—Approximately 11 to 13 cm.

*Average depth.*—Approximately 8 to 10 cm.

*Peduncle length.*—Approximately 17 to 20 cm.

*Pedicel length.*—Approximately 4.0 to 4.4 cm.

*Number of umbels/plant.*—When grown in a 10 cm. pot at 9 weeks after the sticking of a rooted cutting, there commonly are 3 to 5 umbels per plant.

*Number of florets/umbel.*—Approximately 48 to 61.

B. Corolla:

*Average diameter.*—Approximately 5.0 to 5.1 cm.

*Form.*—Single.

*Color.*—General tonality from a distance of three meters: red and white. Adaxial: Red Group 47B at the darkest red point, to Red Group 55C as light pink, to white. Abaxial: Red Group 43C with veins of Red Group 43B on the darkest red petals.

C. Bud:

*Shape.*—Oval pointed.

*Color.*—Each floret tends to exhibit a somewhat unique bud coloration.

D. Reproductive organs:

*Androecium.*—The anthers are commonly approximately 2 mm. in length. The pollen color is Orange-Red Group 33B. The filaments commonly are approximately 4 to 6 mm. in length.

*Gynoecium.*—The pistil length commonly is approximately 7 mm. There is a single stigma which commonly has a length of approximately 3 mm. which commonly branches into 5 parts, and the style length commonly is approximately 4 mm.

*Fertility.*—Usually does not produce fruits in the absence of mechanical fertilization.

E. Spring flowering response period: Approximately 6 to 7 weeks from rooted cuttings under greenhouse conditions.

F. Outdoor flower production: Freely flowering under outdoor growing conditions with substantially continuous blooming.

Durability: Ships well.

PLANT

A. Foliage: Medium green with zone.

*Form.*—Reniform, with cordate base.

*Margin.*—Crenate.

*Color.*—Adaxial: Green Group 137C with a zone of Yellow-Green Group 147A. Abaxial: Yellow-Green Group 147B.

*Size.*—Approximately 10 to 12 cm. at the widest point and approximately 7.5 to 9.5 cm. at the narrowest point.

*Tolerance to Botrytis.*—Good due to the self-cleaning nature of the florets.

B. General appearance and form:

*Internode length.*—Commonly varies from approximately 2 to 3 cm.

*Branching pattern.*—Somewhat basal branching.

*Height.*—Commonly approximately 27 to 31 cm. above a 10 cm. pot at 9 weeks under standard greenhouse conditions.

I claim:

1. A new and distinct cultivar of Geranium plant named Starburst Red substantially as herein shown and described, which:

(a) exhibits single multi-patterned red, white, and pink florets, (b) forms medium green foliage with zonation, and (c) exhibits a medium growth habit.

* * * * *